United States Patent [19]

Ito

[11] Patent Number: 4,666,268
[45] Date of Patent: * May 19, 1987

[54] OPTICAL DEVICE HAVING A FOCUSING FUNCTION

[75] Inventor: Yuji Ito, Chigasaki, Japan

[73] Assignee: Canon Kabushiki Kaisha, Tokyo, Japan

[*] Notice: The portion of the term of this patent subsequent to Mar. 5, 2002 has been disclaimed.

[21] Appl. No.: 875,247

[22] Filed: Jun. 16, 1986

Related U.S. Application Data

[63] Continuation of Ser. No. 717,874, Apr. 1, 1985, abandoned, which is a continuation of Ser. No. 470,201, Feb. 28, 1983, abandoned.

[30] Foreign Application Priority Data

Mar. 5, 1982 [JP] Japan ................................. 57-35632

[51] Int. Cl.⁴ .......................... A61B 3/14; G03B 29/00
[52] U.S. Cl. .................................. 351/206; 351/205; 354/62
[58] Field of Search ................ 350/449; 351/205, 206, 351/207, 415; 354/62

[56] References Cited

U.S. PATENT DOCUMENTS

| 3,784,286 | 1/1974 | Dudrangne | 350/453 |
| 4,235,540 | 11/1980 | Hanamura et al. | 351/206 |
| 4,248,506 | 2/1981 | Takahashi | 351/205 |

Primary Examiner—Rodney B. Bovernick
Assistant Examiner—P. M. Dzierzynski
Attorney, Agent, or Firm—Fitzpatrick, Cella, Harper & Scinto

[57] ABSTRACT

An optical device comprising, in succession from the object side, light beam control system, a stationary optical element having a reduction-imaging function, and a focusing optical element, the optical device being particularly suitable for use with an eye-fundus camera or the like.

9 Claims, 15 Drawing Figures

OPTICAL DEVICE HAVING A FOCUSING FUNCTION

This application is a continuation of application Ser. No. 717,874 filed Apr. 1, 1985, now abandoned, which in turn is a cont. of U.S. patent application Ser. No. 470,201, filed Feb. 28, 1983, which is abandoned.

BACKGROUND OF THE INVENTION

1. Field of the Invention

This invention relates to an optical device which eliminates the difficulties resulting from focusing, and is suitable, for example, as the optical system of an ophthalmologic instrument.

2. Description of the Prior Art

Most optical devices are provided with a portion for achieving the focusing, and as the focusing method, for example, in an eye-fundus camera, there is known a method whereby a camera body containing a film therein is moved relative to the device body, and a method whereby the focusing is realized by movement of the forward portion of a picture-taking lens lying rearwardly of a mirror for introducing an illuminating light or by movement of a lens added to the object side of the picture-taking lens. However, in the case of a device which is provided with a zoom lens or an attachment lens and is capable of magnification changing operation, the method whereby the film is moved is disadvantageous because the focus must be re-adjusted each time the magnification is changed. Accordingly, it is convenient that the focusing portion is disposed on the object side with respect to the lens having a magnification changing function, and in Applicant's prior U.S. application Ser. No. 30,959 now abandoned (see FIG. 1 of the accompanying drawings), a negative focusing lens is provided rearwardly of the photographing stop. In FIG. 1, reference numerals 1 and 2 show an eye to be examined in a model fashion, and 1 designates the eye fundus and 2 denotes the pupil. Reference numeral 3 designates the objective lens of an eye-fundus camera, reference numeral 4 denotes the primary eye-fundus image by the objective lens 3, and reference numeral 5 designates an apertured mirror having an opening in the center thereof. The central opening has the function as a stop, but a separate stop may also be disposed behind this reflecting mirror, and the stop and the pupil 2 or the cornea are conjugate with each other. Designated by 6 is a focusing lens group having a negative power and movable back and forth during focusing. Reference numeral 7 denotes a stationary lens group not for imaging but for aberration correction, reference numerals 8 and 9 designate lens groups movable at the same time and independently of each other during zooming, and reference numeral 10 denotes a positive relay lens group. Reference numeral 11 designates a jump-up mirror which is obliquely disposed during observation and retracted out of the optical path during photography. Reference numeral 12 designates a photographing film, and reference numeral 13 denotes a final eye-fundus image which has been re-imaged by an imaging lens comprising six to ten lenses. Reference numeral 14 designates an optical path changing-over mirror and reference numeral 15 denotes an eyepiece, and these two constitute a finder optical system. A light ray l depicted in a solid line is a principal ray. Relay lens groups 16, 17, a light-intercepting plate 18 having a ring-shaped slit therein, a mirror 19, a condenser lens 20, a photographing light source 21, a condenser lens group 22 and an observation light source 23 together constitute an illuminating system for illuminating the eye to be examined through the apertured mirror 5.

However, in the optical system of the aforementioned prior application, if an attempt is made to cause the light beam to pass effectively in whatever position the focusing lens is, off-axis beams passing through the lenses subsequent to the focusing lens become spaced apart from the optical axis and increase the lens diameters and thus, the thickness of each lens has increased and this has led to an optical system having a great full length. These difficulties have occurred not only in a case where the picture-taking lens is of variable magnification but also in a case where the picture-taking lens is of fixed magnification.

SUMMARY OF THE INVENTION

It is an object of the present invention to make the optical system compact. Such object is achieved by disposing a stationary optical element having an image-reducing function between a photographing stop and an optical element having a focusing function, that is, by disposing, in succession from the object side, light beam control means, a stationary optical element having an image-reducing function, and a focusing optical element.

The invention will become fully apparent from the following detailed description thereof taken in conjunction with the accompanying drawings.

DESCRIPTION OF THE PREFERRED EMBODIMENTS

Figure 2:
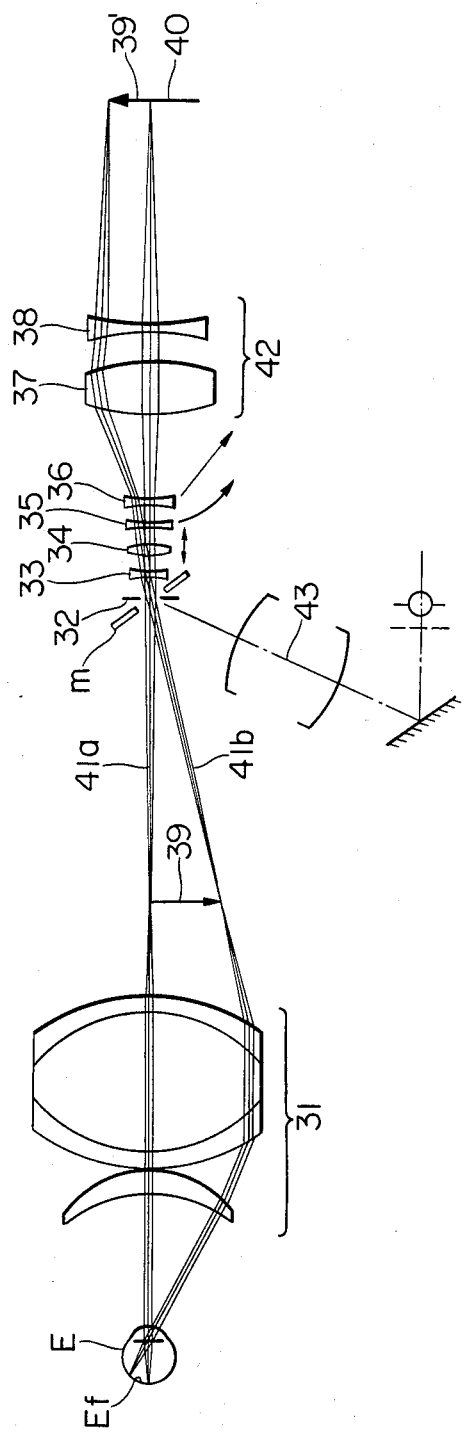
FIG. 2 shows an embodiment of the present invention.

Some embodiments of the present invention will hereinafter be described by reference to the drawings. In FIG. 2, reference character E designates an eye to be examined which is supposed as being in the vicinity of zero diopter. Reference character Ef denotes the eye fundus. Designated by 31 is an objective lens having the function of imaging a light beam from the eye fundus Ef as an image 39. Reference character m denotes an apertured mirror obliquely disposed with respect to the optical axis, and reference numeral 32 designates a stop for limiting a picture-taking or observation light beam. Generally, the apertured mirror m and the stop 32 are proximate to each other. Designated by 33 is a stationary lens of negative refractive power having the function of forming the image 39 on a reduced scale. In the present embodiment, the image is a virtual image. Reference numeral 34 denotes a focusing lens which is movable in the direction of the optical axis for focusing and has a positive refractive power. This focusing lens 34 emits the light beam from the stationary lens 33 as a parallel light beam. Reference numerals 35 and 36 designates a zoom portion. The lens 35 has an image plane movement compensating function and the lens 36 has the function of changing the focal length. In the present embodiment, both of these lenses have a negative refractive power and are movable in the direction of the optical axis at the same time and independently of each other. Designated by 42 is an imaging lens, and a positive lens group 37 and a negative lens group form a telephoto type. Denoted by 40 is a film surface. Reference numeral 43 designates an illuminating optical path having the function of transmitting the optical path to the apertured mirror m.

Figure 1:
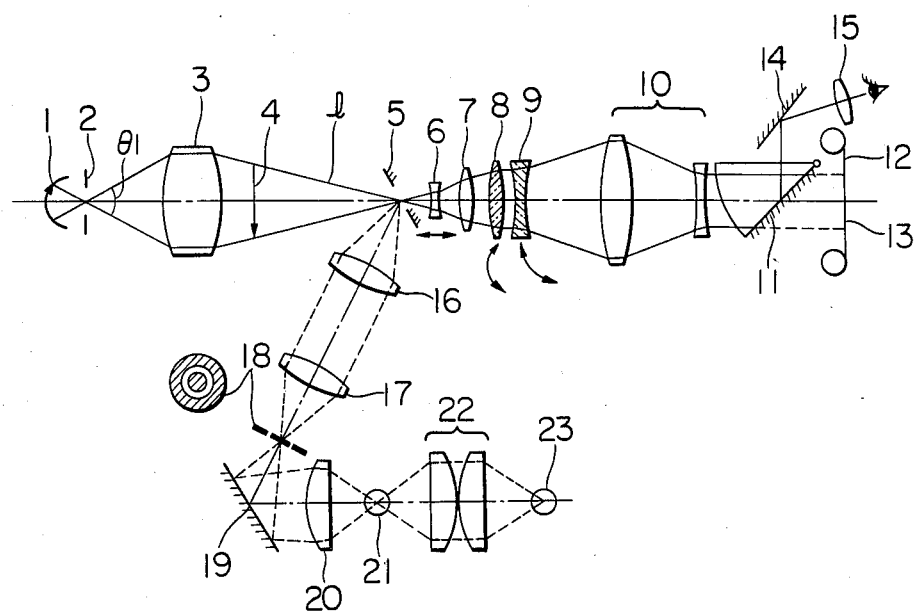
FIG. 1 shows the optical system disclosed in the aforementioned prior U.S. application.

In the illuminating optical path, a ring-like slit similar to that of FIG. 1 is provided at a position optically conjugate with the pupil of the eye to be examined. This ring-like slit, not shown, is also optically conjugate with the apertured mirror m, and the eye to be examined is illuminated in a ringlike form from the marginal portion of the pupil through the apertured mirror m, and the reflected light from the eye fundus is detected not through the apertured mirror m but through the stop 32.

Designated by 41a is an on-axis light beam from the eye fundus, and denoted by 41b is an off-axis light beam. These two light beams are caused to form a real image 39 by the objective lens 31, whereafter they enter the stationary lens 33 under the control of the stop 32 and are subjected to a diverging action thereby. The stationary lens 33 forms a virtual image of the image 39, but since this is a reduced image, the amount of movement is reduced even if the eye to be examined E has abnormality of refractive power and the position at which the image 39 is formed moves. Accordingly, the amount of movement of the focusing lens 34 is reduced, so that the variation thereafter in the optical path resulting from the movement of the focusing lens 34 can be suppressed and the off-axis light rays pass by a low position as compared with a case where they move through a negative lens near the stop. Also, the focusing lens 34 forms an image always at a predetermined position, or in the present embodiment, at infinity, and therefore, the lenses 35 and 36 of the zoom portion may assume desired arrangements. The imaging lens 42 causes the two light beams having left the zoom portion to be imaged on the film surface 40. Designated by 39' is the image thereof. The stationary lens 33 and the focusing lens 34 are selected to opposite refractive powers, but where the stationary lens 33 is selected to a negative refractive power, if it is brought into proximity to the stop, the principal ray can be prevented from being sharply refracted.

In the above-described construction, the constructions subsequent to the stop 32 can be modified variously, and FIGS. 3 to 7 show modified zoom portions. The objective lens 31 and the illuminating optical path are omitted in these Figures.

Figure 3:
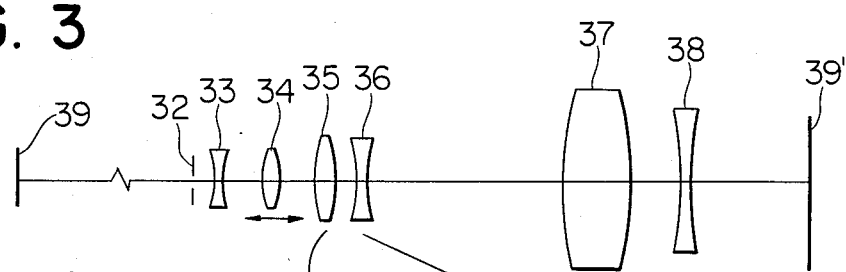
FIGS. 3 to 13B show various modifications.

In FIG. 3, the image plane movement compensating group (compensator) 35 of the zoom portion is endowed with a positive refractive power and it is caused to assume a cam locus different from that in the above-described embodiment relative to the linear movement of the focal length changing group (variator) 36.

Figure 4:
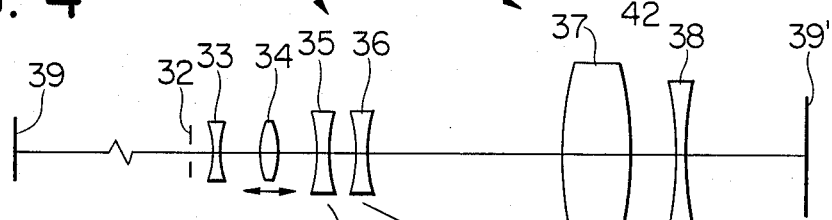

The refractive power of the compensator of FIG. 4 is of the same sign as that described above and this is an example in which the cam locus has been changed.

Figure 5:
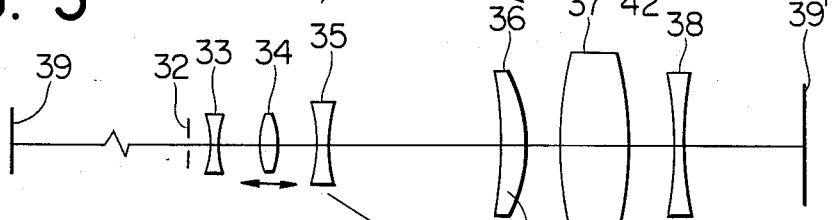

FIG. 5 shows an embodiment in which the order of the compensator and variator is reversed and the variator 35 has a negative refractive power and the compensator 36 has a positive refractive power.

Figure 6:
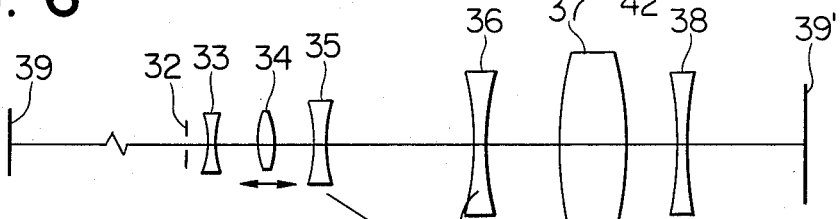

FIG. 6 shows an embodiment in which the refractive power of the compensator 36 is negative with a result that the sense of the cam locus is opposite to that in FIG. 5.

Figure 7:
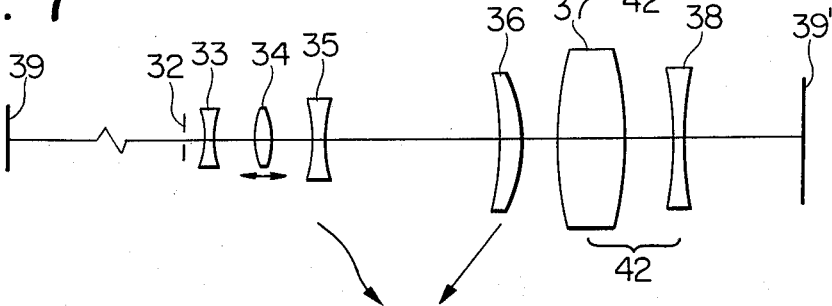
Figure 8:
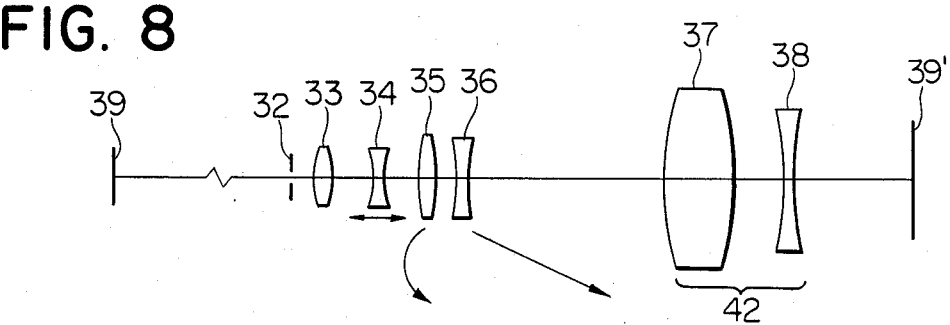
Figure 9:
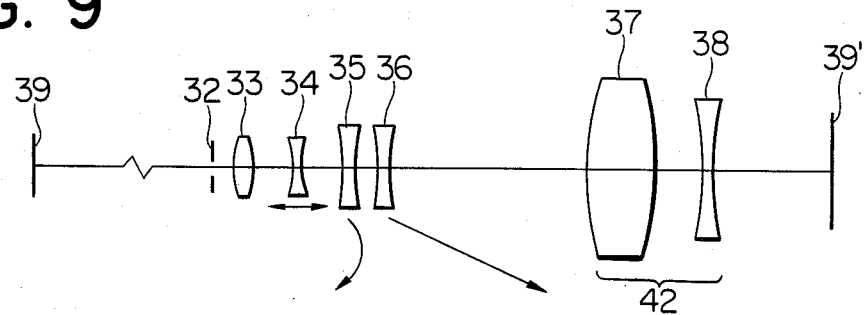
Figure 10:
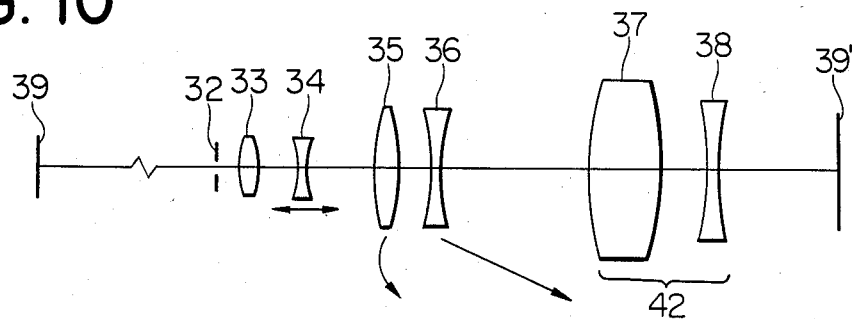
Figure 11:
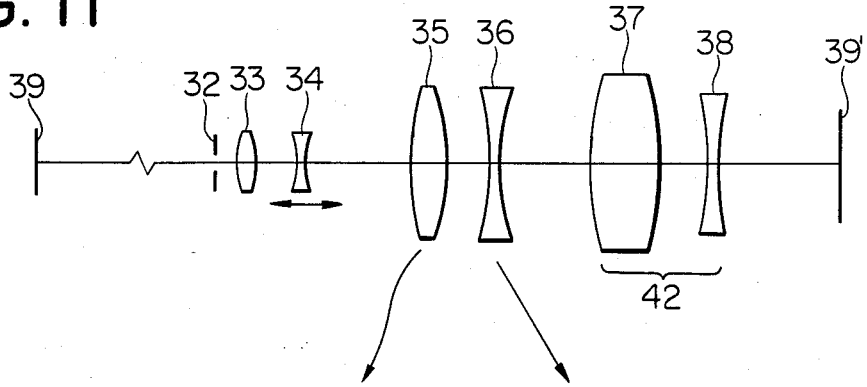

FIG. 7 shows an embodiment in which the cam locus of the variator 35 is non-linear.

As described above, the application of the present invention is not limited in the form of the zoom portion and the refractive power of the stationary lens 33 is neither limited to the negative.

In the embodiments of FIGS. 8 to 11, the refractive power of the stationary lens 33 is positive and therefore, the focusing lens 34 is of a negative refractive power.

Figure 12A:
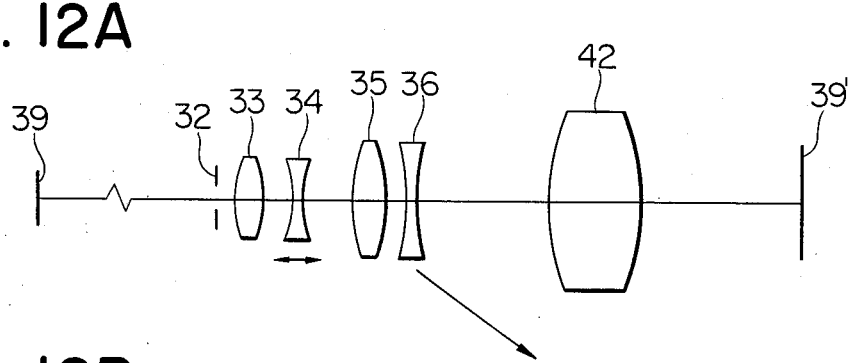
Figure 12B:
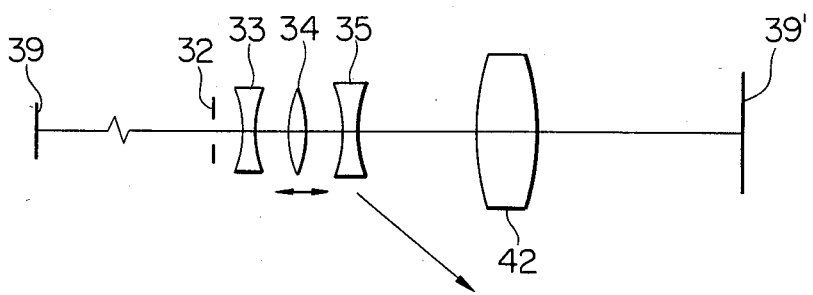

FIGS. 12A and 12B show embodiments which adopt a so-called varifocal portion which lacks the compensator of the zoom portion. The variator 36 of FIG. 12A and the variator 35 of FIG. 12B have their image plane coincident with the film surface at two locations on the optical axis. On the other hand, an ordinary converging lens group is employed as the imaging lens 42.

In FIG. 12A, a positive stationary lens 35' is disposed behind the focusing lens 34, but in some cases, it may be negative in the balance with the refractive power of the focusing lens.

Figure 13A:
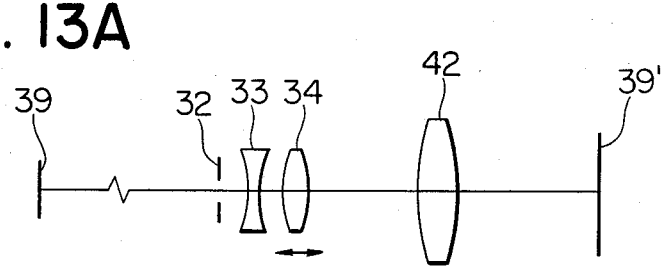
Figure 13B:
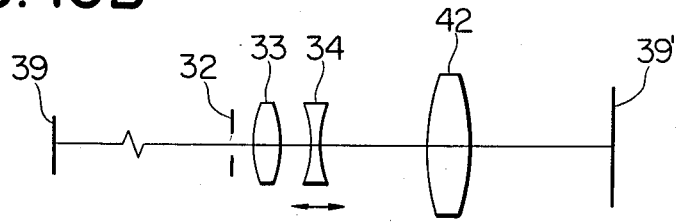

FIG. 13 shows an example of the system which does not have a zoom portion or a varifocal portion. In this example, magnification change is not taken into account, but an attachment lens may be mounted forwardly or rearwardly of the imaging lens 42.

In all of the above-described embodiments, an objective lens exists forwardly of the stop 32 and such a system in which the image by this objective lens is re-imaged is taken into consideration, but the present invention is also applicable to a forward-stop system having no objective lens. In the foregoing, various modifications have been considered, but among them, the most effective is the optical system described in connection with FIG. 2, that is, the system in which the objective lens, the stop, the negative stationary lens, the positive focusing lens, the zoom portion comprising two negative groups, and the telephoto type imaging lens are disposed in the named order.

According to the present invention as described above, the off-axis light beam can be prevented from being greatly spaced apart from the optical axis and therefore, the diameters of the subsequent lens groups or the full length of the system can be reduced and this is convenient for making the device compact and light in weight as well as very effective for reducing the cost.

What I claim is:

1. An ophthalmologic apparatus for focusing an image of the fundus of an eye to be examined, comprising in succession from the eye:
    an objective lens adapted to be positioned facing the eye to be examined and to form an intermediate image of the fundus at a position which is movable in accordance with the refractive power of the eye;
    light beam control means provided at a position optically conjugate with the pupil of the eye with respect to said objective lens; and
    an image optical system for focusing said intermediate image of the fundus of the eye onto a predetermined image plane through said light beam control means, wherein said imaging optical system includes, in succession from the eye, an image-reducing optical element having an image-reducing function and a focusing optical element, said image-reducing optical element being stationary relative to said light beam control means and said focusing optical element being movable along the optical axis thereof relative to said image-reducing optical element to form a focused fundus image of the eye at said image plane, and the range of movement of said focusing optical element being reduced by said image-reducing optical element.

2. An ophthalmologic apparatus according to claim 1, further comprising another optical element for magnification change.

3. An ophthalmologic apparatus according to claim 1, wherein said image-reducing optical element and said focusing optical element have refractive powers of opposite tendencies.

4. An ophthalmologic apparatus according to claim 1, wherein said light beam control means comprises an apertured mirror, said mirror being provided with a central aperture and a ring-like marginal mirror portion, the eye being illuminated through said mirror portion.

5. An ophthalmologic apparatus according to claim 1, wherein said focusing optical element emits the light beam from said image-reducing optical element as a parallel light beam.

6. An ophthalmologic apparatus for focusing an image of the fundus of an eye to be examined, comprising in succession from the eye;
   an objective lens adapted to be positioned facing the eye to be examined and to form an intermediate image of the fundus at a position which is movable in accordance with the refractive power of the eye;
   light beam control means provided at a position optically conjugate with the pupil of the eye with respect to said objective lens; and
   an imaging optical system for focusing said intermediate image of the fundus of the eye onto a predetermined image plane through said light beam control means, wherein said imaging optical system includes, in succession from the eye, an image-reducing optical element having a negative refractive power to project said intermediate image at a reduced magnification and a focusing optical means, said image-reducing optical element being stationary relative to said light beam control means and the condition of said focusing optical means being variable relative to said image-reducing optical element to form a focused fundus imaage of the eye at said image plane.

7. An ophthalmologic apparatus for focusing an image of the fundus of an eye to be examined, comprising in succession from the eye:
   an objective lens adapted to be positioned facing the eye to be examined and to form an intermediate image of the fundus at a position which is movable in accordance with the refractive power of the eye;
   light beam control means provided at a position optically conjugate with the pupil of the eye with respect to said objective lens; and
   an imaging optical system for focusing said intermediate image of the fundus of the eye onto a predetermined image plane through said light beam control means, wherein said imaging optical system includes, in succession from the eye, an image-reducing optical element having an image-reducing function and a focusing optical means, said image-reducing optical element being stationary relative to said light beam control means and the condition of said focusing optical means being variable relative to said image-reducing optical element to form a focused fundus image of the eye at said image plane.

8. An ophthalmologic apparatus according to claim 6, wherein said focusing optical means emits the light beam from said image-reducing optical element as a parallel light beam.

9. An ophthalmologic apparatus according to claim 7, wherein said focusing optical means emits the light beam from said image-reducing optical element as a parallel light beam.

* * * * *